United States Patent [19]

Rogers et al.

[11] 4,362,743
[45] Dec. 7, 1982

[54] ANTIBACTERIAL MONIC ACID ESTERS

[75] Inventors: Norman H. Rogers, Horsham; Peter J. O'Hanlon, Redhill; Graham Walker, Guildford, all of England

[73] Assignee: Beecham Group Limited, England

[21] Appl. No.: 289,103

[22] Filed: Jul. 31, 1981

[30] Foreign Application Priority Data

Aug. 2, 1980 [GB] United Kingdom ............... 8025400

[51] Int. Cl.³ ................... A61K 31/35; C07D 309/06
[52] U.S. Cl. .................................. 424/283; 542/426; 542/427; 424/275; 424/274; 424/267; 424/263; 424/256; 549/414; 549/417
[58] Field of Search ............... 260/345.8 R; 542/426, 542/427; 424/283, 275, 274, 267, 263, 256

[56] References Cited

U.S. PATENT DOCUMENTS

| | | | |
|---|---|---|---|
| 3,726,983 | 7/1973 | Weinshenker et al. | 424/283 |
| 4,102,901 | 7/1978 | Luk et al. | 260/345.8 R |
| 4,166,863 | 1/1978 | Luk | 424/283 |
| 4,206,224 | 7/1978 | Clayton | 424/283 |
| 4,248,887 | 3/1979 | Rogers et al. | 424/283 |

FOREIGN PATENT DOCUMENTS 2037770  7/1980  United Kingdom.
2009154  6/1982  United Kingdom.

*Primary Examiner*—Nicky Chan
*Attorney, Agent, or Firm*—Jacobs & Jacobs

[57] ABSTRACT

Compounds of formula (II):

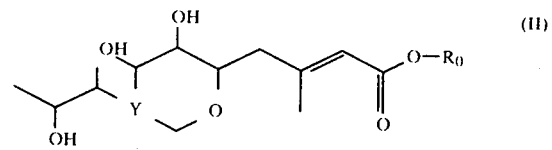

in which Y represents

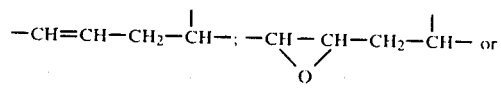

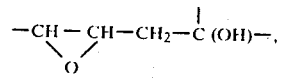

and $R_0$ represents a $C_{2-20}$ alkyl, $C_{3-8}$ cycloalkyl, $C_{4-20}$ alkenyl, arakyl, cycloalkylalkyl, heterocyclyl or heterocyclylalkyl group, which is substituted by a hydroxyiminohydrazono- or semicarbazono group, have activity against human and veterinary bacteria and mycoplasma. They may be produced by conventional methods and are used in conventional formulations.

7 Claims, No Drawings

ANTIBACTERIAL MONIC ACID ESTERS

This invention relates to antibacterial compounds and in particular to a class of monic acid derivatives which have antibacterial activity against certain Gram-positive and Gram-negative organisms, and also possess anti-mycoplasmal activity. The Compounds are therefore of value in the treatment of human and veterinary infections.

The compounds of formula (I) and salts and esters thereof:

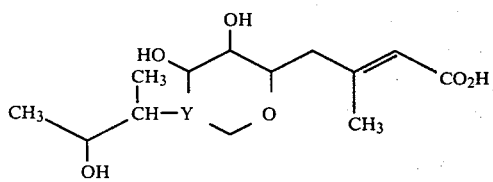
(I)

wherein Y represents

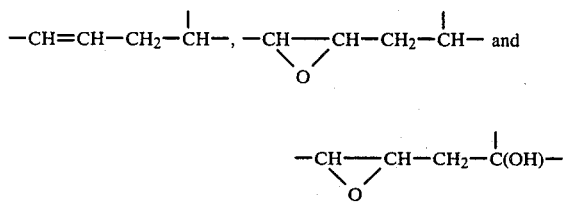

are disclosed in West German Offenlegungsschriften No. 2726619, 2726618 and 2848687 and European Patent Application No. 79300371.6. Compounds of formula (I) having the tri-substituted double bond in the E-configuration are referred to as monic acid C, monic acid A and monic acid B respectively.

According to the present invention there is provided a compound of the formula (II):

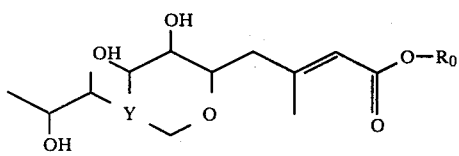
(II)

in which Y is as defined with respect to formula (I) and $R_0$ represents a $C_{2-20}$ alkyl, $C_{3-8}$ cycloalkyl, $C_{4-20}$ alkenyl, aralkyl, cycloalkylalkyl, heterocyclyl or heterocyclylalkyl group which is substituted by a hydroxyimino-, hydrazono- or semicarbazono-group, each of which is optionally substituted by one or more $C_{1-6}$ alkyl or aryl groups. In addition, the $C_{1-6}$ alkyl and aryl groups may be optionally substituted by, for example, one or more bromine atoms or $NO_2$ groups.

Suitable aralkyl groups are phenylalkyl groups such as benzyl or phenylbutyl. Preferred heterocyclic groups are 5 or 6 membered heterocyclic rings, optionally substituted by lower alkyl, containing an oxygen, sulphur or nitrogen hetero-atom. Suitable examples of such groups are thienyl and furyl.

Preferably $R_0$ represents a group of the formula (III):

in which W represents a

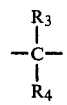

group where $R_3$ and $R_4$ are the same or different and each is a hydrogen atom or a $C_{1-4}$ alkyl, aryl or aralkyl group, Z represents a $-(CH_2)_n-$ group, where n is an integer of from 1 to 10 or is zero, or a $-C_6H_4-$ group, $R_1$ represents a hydroxyimino, hydrazono or semicarbazono group each of which is optionally substituted by one or more $C_{1-6}$ alkyl or aryl groups and $R_2$ represents a hydrogen atom, a $C_{1-4}$ alkyl, aryl or heterocyclyl group.

The compound (II) of this invention incorporates a tri-substituted double bond and may therefore exist in both the E (natural) and Z (or iso) geometrical forms. It is to be understood that both geometrical isomers of the compound of formula (II) are included within the scope of this invention, as well as mixtures of the two isomers. However, because in general the E-isomer of a particular derivative of compound (II) has the greater activity, it is preferable to employ that isomer.

In addition, the 10, 11 double bond in the C-series of compounds is naturally E in configuration.

Similarly, the $-C=R_1$ double bond of formula (III) can give rise to E and Z isomerism about this bond, and the invention includes within its scope both of these isomers as well as mixtures thereof.

Compounds of this invention have antibacterial and antimycoplasmal activity, and are therefore of value in the treatment of bacterial and mycoplasma-induced human and veterinary diseases.

The infections against which compounds of this invention are particularly useful include venereal disease. They are also effective in the treatment of respiratory infections such as bacterial bronchitis; and bacterial meningitis, non-specific urethritis and pneumonia. In animals it may be employed for the treatment of mastitis in cattle, for swine dysentery, and for mycoplasma infections in animals such as turkeys, chickens, pigs and cattle.

Some of the human and veterinary diseases either caused by mycoplasma species or in which they play a prominent role, and against which compounds of this invention are effective, are as follows:

| | |
|---|---|
| Avian | |
| M. gallisepticum | Chronic respiratory diseases (airsacculitis) of chickens and turkeys. |
| Bovine | |
| M. bovis | Mastitis, respiratory disease and arthritis of cattle. |
| M. dispar | Calf pneumonia |
| Porcine | |
| M. suipneumoniae | Enzootic pneumonia of pigs |
| M. hyorhinis ⎫ | |
| | arthritis in pigs |
| M. hyosynoviae ⎭ | |
| Human | |

| | |
|---|---|
| *M. pneumoniae* | primary atypical pneumonia |

Compounds of the present invention are particularly useful in the treatment of enzootic pneumonia in animals such as pigs, cattle and sheep, because they also have activity against the bacteria, *Bordetella bronchiseptica, Pasteurella multocida* and Haemophilus spp, which often cause respiratory complications in cases of this disease.

This invention also provides a pharmaceutical or veterinary composition which comprises a compound of formula (II) together with a pharmaceutically or veterinary acceptable carrier or excipient.

The compositions may be formulated for administration by any route, and would depend on the disease being treated. The compositions may be in the form of tablets, capsules, powders, granules, lozenges, liquid or gel preparations, such as oral, topical or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin compounds of this invention may be made up into a cream, lotion or ointment. Cream or ointment formulations that may be used for compounds of formula (II) are conventional formulations well known in the art, for example, as described in standard text books of pharmaceutics and cosmetics, such as Harry's Cosmeticology published by Leonard Hill Books, and the British Pharmacopoeia.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can either be suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability the composition can be frozen after filling into the vial and water removed under vacuum. The dry lypophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compounds.

Veterinary compositions for intrammary treatment of mammary disorders in animals, especially bovine mastitis, will generally contain a suspension of a compound of formula (II) in an oily vehicle.

The compositions may contain from 0.1% to 99% by weight, preferably from 10-60% by weight, of the active material, depending on the method of administration. Where the compositions comprise dosage units, each unit will preferably contain from 50-500 mg, of the active ingredient. The dosage as employed for adult human treatment will preferably range from 100 mg to 3 g, per day, for instance 250 mg to 2 g, per day, depending on the route and frequency of administration.

Alternatively a compound of formula (II) may be administered as part of the total dietary intake. In this case the amount of compound employed may be less than 1% by weight of the diet and in preferably no more than 0.5% by weight. The diet for animals may consist of normal foodstuffs to which the compound may be added or it may be added to a premix.

A suitable method of administration of a compound of formula (II) to animals is to add it to the animals drinking water. In this case a concentration of compound in the drinking water of about 5–500 µg/ml, for example 5–200 µg/ml, is suitable.

The compounds of formula (II) may be prepared by reacting a compound of formula (IV):

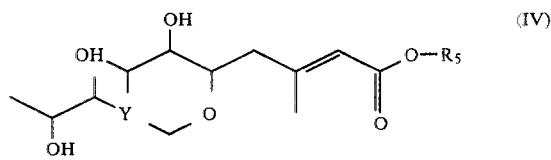

in which Y is as defined in relation to formula (I) and $R_5$ represents a $C_{2-20}$ alkyl, $C_{3-8}$ cycloalkyl, $C_{4-20}$ alkenyl, aralkyl, cycloalkylalkyl, heterocyclyl or heterocyclylalkyl group substituted by an oxo group, with hydroxylamine, hydrazine or semicarbazide, each of which is optionally substituted by one or more $C_{1-6}$ alkyl or aryl groups which may themselves be optionally substituted by, for example, one or more bromine atoms or $NO_2$ groups.

The reaction is suitably carried out in an aqueous lower alkanolic solvent, preferably buffered aqueous methanol or ethanol at ambient temperature, and the compound of formula (II) extracted from the reaction mixture with an organic solvent. Alternatively, the reactants can be refluxed with a lower alkanol in pyridine.

One example of a substituted hydrazine is Girards Reagent T ($NH_2NHCOCH_2N^+Me_3Cl^-$) or Reagent P

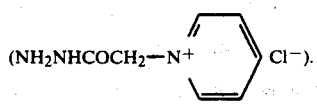

The compounds of formula (II) may also be prepared by reacting a compound of formula (V):

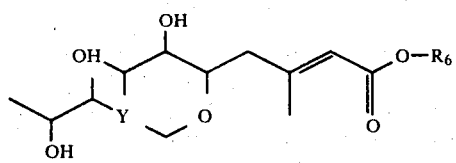

in which Y is as defined in relation to formula (I) and $R_6$ represents an alkali metal atom, such as sodium, with a compound of formula (VI):

$$R_0\text{-}X \qquad (VI)$$

in which $R_0$ is as defined in relation to formula (II) and X is a leaving group such as a halogen atom or an alkyl or aryl sulphonate group, preferably a chlorine, bromine or iodine atom, or a mesylate group.

The reaction is suitably carried out in polar aprotic solvents such as dimethylformamide (DMF) or dimethyl acetamide (DMAc) with or without a trace of hexamethylphosphorotriamide (HMPT) at 0°-150° C., preferably 20°-80° C., for 2-18 hours.

The compounds of formula (VI) may conveniently be prepared by reaction a compound of formula (VII):

$$R_5\text{-}X \qquad (VII)$$

in which $R_5$ is as defined in relation to formula (IV) and X is as defined in relation to formula (VI), with hydroxylamine, hydrazine or semicarbazide optionally substituted with at least one $C_{1-6}$ alkyl or aryl group.

This reaction is suitably carried out in a buffered aqueous alkanolic solvent, preferably aqueous methanol or ethanol with for example NaOAc, heated under reflux or alternatively an alkanolic solvent, such as methanol or ethanol and pyridine heated under reflux.

However, the reaction is not suitable for the production of unsubstituted oximes and unsubstituted hydrazones when the $R_5$ radical contains a

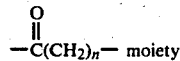

attached to the leaving group X via a $CH_2$ group, and wherein n is 2 or 3, since intramolecular cyclisation then tends to occur.

An alternative process for the preparation of compounds of formula (II) comprises reacting a monic acid mixed anhydride with a compound of formula $R_0OLi$ or $R_0OMgX$, in which $R_0$ is defined with respect to formula (II). This process is only suitable for $R_0$ radicals which do not contain acidic protons.

Prior to the above processes of this invention, it may be desirable to protect the hydroxyl groups in compounds of formulae (IV) and (V). Although reaction is possible without hydroxyl protection, in some cases higher yields could be formed if the hydroxyl groups were protected. Such protecting groups must be removable under suitably mild conditions and suitable groups include silyl groups produced from a silylating agent. Particularly suitable hydroxyl-protecting groups include tri-methylsily, t-butyldimethylsilyl, methylthiomethyl, β-methoxyethoxymethyl.

It is also possible to protect the glycol moiety in compounds of formulae (IV) and (V) and suitable reagents for forming such a hydroxyl-protecting group include compounds of formula (VIII):

wherein $R^8$ is hydrogen or a $C_{1-6}$ alkyl group and $R^9$, $R^{10}$ and $R^{11}$ independently represent a $C_{1-6}$ alkyl group.

The group $R^8$ may be for example hydrogen, methyl, ethyl, n- or iso-propyl. Most suitably, $R^8$ represents hydrogen so that the compound of formula (VIII) is a trialkyl orthoformate.

Groups $R^9$, $R^{10}$ and $R^{11}$ may be for example, methyl, ethyl, n- or iso-propyl, n-, iso-, sec- or tert-butyl. Preferably $R^9$, $R^{10}$ and $R^{11}$ are all the same and each represents a methyl group.

Other glycol protecting groups which are suitable for the case where Y in formula (II) is $-CH=CH-CH_2-CH-$ include those wherein the glycol moiety is converted to the structure:

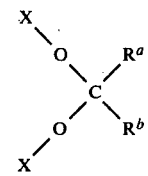

where $R^a$ and $R^b$ are hydrogen, $C_{1-6}$ alkyl, or phenyl, or together form a carbocyclic ring, preferably a cyclohexylidene ring. Preferably $R^a$ and $R^b$ are both methyl, i.e. the group is the isopropylidene group. This group may be introduced by reaction with 2,2-dimethoxypropane, and removed by treatment with 2,2-dimethoxypropane, and removed by treatment with acetic acid.

The hydroxy-protecting group may be removed by a conventional method for the particular hydroxy-protecting group.

The following Examples illustrate the preparation of a number of compounds of the present invention.

EXAMPLE 1

4-Hydroxyimino-4-phenylbutyl monate A

A solution of 4-oxo-4-phenylbutyl monate A (50 mg, 0.1 mmol), hydroxylamine hydrochloride (35 mg, 0.5 mmol), and ammonium acetate (40 mg, 0.5 mmol) in water (10 ml) and methanol (10 ml), was stirred at 20° for 22 h. Water and salt were then added and the mixture extracted four times with methylene chloride. The combined organic extracts were dried and evaporated in vacuo to leave an oil (50 mg), which was purified by chromatography on silica gel, eluting with 0 to 4% methanol in chloroform. 4-Hydroxyimino-4-phenylbutyl monate A was obtained as an oil (30 mg, 60%), $\nu_{max}$1710, 1645, 915 cm$^{-1}$; $\lambda_{max}$225 nm ($\epsilon_m$15,500); $\delta_H$(CDCl$_3$) 7.3-7.8 (5H, m, aryl), 5.80 (1H, s, H2), 2.19

(3H, s, CH$_3$-15), 1.19 (3H, d, CH$_3$-14), 0.92 (3H, d, CH$_3$-17); δ$_C$ (CDCl$_3$) 166.9 (C1), 158.9 (C4'), 157.2 (C3), 135.6, 129.3, 128.2, 126.4 (aryl), 117.6 (C2), 75.0 (C5), 71.3 (C13), 70.5 (C7), 69.1 (C6), 65.5 (C16), 63.5 (C1'), 61.3 (C11), 55.8 (C10), 42.8 (C4, C12), 39.6 (C8), 31.6 (C9), 25.6 (C3'), 23.1 (C2'), 20.8 (C14), 19.3 (C15), 12.7 (C17); m/e (relative intensity) 505 (M$^+$, 1%), 227 (24), 162 (100) (Found: 505.2653. C$_{27}$H$_{39}$NO$_8$ requires 505.2675).

EXAMPLE 2

4-Phenyl-4-semicarbazonobutyl monate A

Method (a)

(i) 4-Chloro-1-phenylbutan-1-one semicarbazone

A mixture of semicarbazide hydrochloride (1.5 g, 10 mmol), anhydrous sodium acetate (1.65 g, 20 mmol), 4-chloro-1-phenylbutan-1-one (1.46 g, 8 mmol), water (10 ml), and ethanol (30 ml) was stirred at 20° for 2 h and then more water (30 ml) was added and the mixture left to crystallise for 16 h at 5°. Filtration then gave the semicarbazone as colourless rhombs which were dried and triturated with ether to give the pure semicarbazone as a white powder, (0.9 g, 47%). mp 132°-134°, ν$_{max}$ (KBr) 3470, 1680, 1575, 1460 cm$^{-1}$; λ$_{max}$ (EtOH) 207 nm (ε$_m$ 23,800), 276 nm (ε$_m$ 26,700); δ$_H$(CDCl$_3$)9.75 (1H, 5, NH), 7.3-7.5, 7.6-7.8 (5H, 2m, aryl), 5.95 (2H, bs, NH$_2$), 3.70 (2H, t, H4), 2.90 (2H, m, H2), 2.00 (2H, m, H3).

(ii) 4-Phenyl-4-semicarbazonobutyl monate A

A mixture of sodium monate A (1.1 g, 3 mmol), 4-chloro-1-phenylbutan-1-one semicarbazone (0.7 g, 3 mmol), sodium iodide (0.5 g), hexamethylphosphoramide (2 drops), and N,N-dimethylformamide (25 ml) was heated at 80° for 16 hours. The mixture was cooled and taken up in ethyl acetate and the solution washed with brine, aqueous sodium bicarbonate, brine, dried (MgSO$_4$) filtered, and evaporated in vacuo. The residue was purified by chromatography using silica (20 g) and 0 to 5% methanol in chloroform. This gave pure product as a colourless oil (47 g, 3%); ν$_{max}$(CHCl$_3$) 1690, 1560, 780, 725 cm$^{-1}$; λ$_{max}$ (EtOH) 218 nm (ε$_m$ 15,300), 275 nm (ε$_m$ 8,800); δ$_H$(CDCl$_3$) 8.60 (1H, 5, NH), 7.3-7.7 (5H, m, aryl), 5.93 (2H, bs, NH$_2$), 2.21 (3H, s, CH$_3$-15), 1.79 (3H, d, CH$_3$-14), 0.91 (3H, d, CH$_3$-17); δ$_C$(CDCl$_3$) 166.1 (Cl), 159.3 (C4'), 157.9 (C3), 149.4 (NHCONH), 136.8 (aryl, C1), 129.4 (aryl C2, C6) 128.7 (aryl C3, C5), 126.1 (aryl C4), 116.2 (C2), 75.2 (C5), 71.2 (C13), 70.7 (C7), 68.4 (C6), 65.6 (C16), 62.2 (C1'), 61.2 (C11), 55.7 (C10), 42.8 (C4, C12), 39.4 (C8), 31.9 (C9), 25.2 (C3'), 22.9 (C2'), 20.8 (C14), 19.9 (C15), 12.6 (C17); m/e (relative intensity) 530 (M+NH$_3$, 8%), 227 (25), 160 (100) (Found: 530.2616, C$_{28}$H$_{38}$N$_2$O$_8$ requires 530.2602).

Method (b)

A mixture of 4-oxo-4-phenylbutyl monate A (0.20 g, 0.4 mmol), semicarbazide hydrochloride (0.06 g, 0.5 mmol) anhydrous sodium acetate (0.08 g, 1.0 mmol), water (5 ml), and ethanol (10 ml), was stirred at 20° for 22 h. The reaction was then poured into brine and extracted four times with dichloromethane. The combined organic fractions were dried (MgSO$_4$) and evaporated in vacuo to leave an oil which was purified by chromatography on silica gel to give first, unchanged starting ketone, (60 mg 30), and then pure semicarbazone (50 mg, 23%), as a colourless and viscous oil, which was identical to that obtained by method (a).

EXAMPLE 3

4-Hydroxyiminocyclohexyl monate A

A solution containing 4-oxocyclohexyl monate A (0.27 g, 0.6 mmol), hydroxylammonium chloride (0.24 g, 3.5 mmol), ammonium acetate (0.27 g, 3.5 mmol), water (30 ml), and methanol (30 ml) was allowed to stand 16 h at 20°, poured into brine, and the resulting mixture extracted three times with dichloromethane. The combined extracts were dried (MgSO$_4$), evaporated in vacuo, and the residue obtained was purified by chromatography on silicagel (10 g), eluting with 0-4% methanol in chloroform, to give the oxime as a colourless oil (0.25 g, 92%), ν$_{max}$(film) 3400b, 1710, 1645, 1240 cm$^{-1}$; λ$_{max}$ (EtOH) 222 nm (ε$_m$ 12,500); δ$_H$ (CD$_3$OD) 5.72 (1H, s, H2), 4.9 (1H, m, H1'), 2.20 (3H, s, CH$_3$-15), 1.19 (3H, d, CH$_3$-14), 0.90 (3H, d, CH$_3$-17); m/e (relative intensity) 455 (M$^+$, 1%), 227 (12), 112 (71), 41 (100) (Found: 455.2563, C$_{23}$H$_{37}$NO$_8$ requires 455.2609).

EXAMPLE 4

4-Hydroxyimino-4-(2-thienyl)butyl monate A

A solution containing 4-oxo-4-(2-thienyl)butyl monate A (0.25 g, 0.5 mmol), hydroxylamine hydrochloride (0.17 g, 2.5 mmol), methanol (50 ml), and 0.05 M aq. ammonium acetate (50 ml) was stirred at 20° for 3 days. Water and salt were then added and the mixture extracted four times with dichloromethane. The combined organic extracts were dried (MgSO$_4$) and evaporated in vacuo to leave an oil which was purified by chromatography on silicagel (10 g), eluting with 0-4% methanol in chloroform, to give the oxime as a colourless oil (0.12 g, 46%), ν$_{max}$ (CHCl$_3$) 3360b, 1705, 1215, 1050 cm$^{-1}$; δ$_H$ (CDCl$_3$) 7.2-7.3, 7.0-7.05 (3H, 2m, thienyl H), 5.86 (1H, s, H2), 4.16 (2H, t, H1'), 2.21 (3H, s, CH$_3$-15), 1.17 (3H, d, CH$_3$-14), 0.93 (3H, d, CH$_3$-17); δ$_C$ (CDCl$_3$) 166.7 (C1), 156.9 (C3), 154.9 (C4'), 139.7, 127.2, 126.9, 126.3 (thienyl C's), 117.7 (C2), 75.1 (C5), 71.4 (C13), 70.6 (C7), 69.1 (C6), 65.5 (C16), 63.4 (C1'), 61.4 (C11), 55.7 (C10), 42.9 (C4, C12), 39.6 (C8), 31.8 (C9), 26.0 (C3'), 23.7 (C2'), 20.8 (C14), 19.3 (C15), 12.7 (C17); m/e (relative intensity) 511 (M$^+$, 1%), 227 (38), 167 (100) (Found: 511.2246. C$_{25}$H$_{37}$NO$_8$S requires 511.2253.

EXAMPLE 5

4-Methoxyimino-4-phenylbutyl monate A

A mixture of 1-chloro-4-phenylbutan-4-one (1.83 g, 10 mmol), O-methylhydroxylammonium chloride (1.67 g, 20 mmol), pyridine (1.21 ml, 15 mmol), and ethanol (15 ml) was heated at reflux for 1 hour and then evaporated in vacuo. The residue was partitioned between chloroform and water, and the organic layer was dried (MgSO$_4$) and evaporated in vacuo to give 1-chloro-4-phenylbutan-4-one O-methyloxime (1.78 g, 84%), ν$_{max}$(neat) 2930, 1445, 1050, 900 cm$^{-1}$; λ$_{max}$ (EtOH) 209 nm (ε$_m$ 17,200), 253 nm (ε$_m$ 11,100); δ$_H$ (CDCl$_3$) 7.3-7.8 (5H, m, aryl), 3.9 (3H, s, OMe), 3.5 (2H, t, H1), 2.9 (2H, t, H3), 2.0 (2H, qn, H2).

A mixture of sodium monate A (1.38 g, 4 mmol), 1-chloro-4-phenyl-butan-4-one O-methyloxime (0.85 g, 4 mmol), and DMF (30 ml) was then stirred together for 16 h at 80°. The mixture was evaporated in vacuo and the residue dissolved in ethyl acetate; this was washed with aqueous sodium bicarbonate and then brine, dried (MgSO$_4$) and evaporated in vacuo. Purification of the residue by chromatography on silicagel (10 g) eluting with 0-4% methanol in chloroform then gave the ester as a colourless oil (0.89 g, 43%), $\nu_{max}$ 3440b, 1710, 1645, 765 cm$^{-1}$; $\nu_{max}$ 215 nm ($\epsilon_m$ 22,000); $\delta_H$(CDCl$_3$) 7.55-7.65, 7.3-7.4 (5H, 2m, aryl), 5.73 (1H, s, H2), 4.09 (2H, t, H1'), 3.95 (3H, s, OCH$_3$), 2.20 (3H, s, CH$_3$-15), 1.19 (3H, d, CH$_3$-14), 0.93 (3H, d, CH$_3$-17); $\delta_C$(CDCl$_3$) 166.7 (C1), 157.7 (C3), 156.9 (C4'), 135.5, 129.1 128.5, 126.3 (aryl), 117.5 (C2), 75.0 (C5), 71.2 (C13), 70.3 (C7), 69.0 (C6), 65.4 (C16), 63.3 (C1'), 61.8 (OMe), 61.2 (C11), 55.5 (C10), 42.9 (C12), 42.8 (C4), 39.5 (C8), 31.6 (C9), 25.7 (C3'), 23.3 (C2'), 20.7 (C14), 19.1 (C15), 12.6 (C17); m/e (relative intensity) 519 (M$^+$, 6%), 488 (15), 275 (12), 175 (100) (Found: 519.2836, C$_{28}$H$_{41}$NO$_8$ requires 519.2842).

EXAMPLE 6

6-Dimethylhydrazonohexyl monate A

A solution containing 5-formylpentyl monate A (0.55 g, 1.25 mmol), N,N-dimethylhydrazine (3.8 ml, 50 mmol), and dry ethanol (12.5 ml) was heated at reflux for 2 h and then evaporated in vacuo. The residue was purified by chromatography (0 to 10% methanol in dichloromethane, 10 g silicagel) to give the hydrazone as a pale brown oil; (0.45 g, 74%) $\nu_{max}$(film) 3400, 1710, 1645, 1450 cm$^{-1}$; $\lambda_{max}$ (EtOH) 224 nm ($\epsilon_m$15,900); $\delta_H$ (CD$_3$OD) 6.8 (1H, t, H6'), 5.7 (1H, s, H2), 4.0 (2H, t, H1'), 2.6 (6H, s, NMe), 2.1 (3H, s, CH$_3$-15), 1.2 (3H, d, CH$_3$-14), 0.9 (3H, d, CH$_3$-17); $\delta_C$ (CDCl$_3$) 166.8 (C1), 156.8 (C3), 139.6 (C6'), 117.5 (C2), 74.9 (C5) 71.0 (C13), 70.3 (C7), 68.8 (C6), 65.4 (C16), 63.6 (C1'), 61.1 (C11), 55.5 (C10), 43.3 (NMe$_2$), 42.9 (C12), 42.7 (C4), 39.5 (C8), 32.7 (C5'), 31.6 (C9), 28.5 (C2'), 27.2 (C4'), 25.5 (C3'), 20.7 (C14), 19.1 (C15), 12.5 (C17); m/e (relative intensity) 484 (M$^+$, 72%), 240 (38), 86 (84) (Found: M$^+$=484.3152, C$_{25}$H$_{44}$N$_2$O$_7$ requires 484.3148).

EXAMPLE 7

5-Hydroxyiminomethylfurfuryl monate A

A solution containing 5-formylfurfuryl monate A (0.110 g, 0.25 mmol), hydroxylammonium chloride (0.085 g, 1.25 mmol), methanol (25 ml) and 0.05 M aqueous ammonium acetate (25 ml) was stirred for 16 h at 20° and then extracted with dichloromethane. The extract was dried (MgSO$_4$) and evaporated in vacuo, and the residue purified by chromatography (10 g silica, 0 to 10% methanol in dichloromethane) to give the oxime as a colourless oil (0.050 g, 43%), identified as a 3:1 mixture of E and Z isomers; $\nu_{max}$ (film), 3380, 1715, 1645, 1220 cm$^{-1}$; $\lambda_{max}$ (EtOH) 221 nm ($\epsilon_m$ 12,400), 273 nm ($\epsilon_m$ 14,900); $\delta_H$ (CD$_3$OD) Major isomer: 7.95 (1H, s, CH=N), 6.63 (1H, d, H4''), 6.52 (1H, d, H3''), Minor isomer: 7.40 (1H, s, CH=N), 7.23 (1H, d, H4''), 6.58 (1H, d, H3''), Both isomers: 5.76 (1H, s, H2), 5.10 (2H, s, H1'), 2.20 (3H, s, CH$_3$-15), 1.20 (3H, d, CH$_3$-14), 0.90 (3H, d, CH$_3$-17); $\delta_C$ (CCDl$_3$) 167.4 (C1), 160.3, 160.2 (C1), 152.9, 151.9 (C2'), 149.9, 147.3 (CH=N), 140.7, 137.1 (C5'), 118.9, 117.6 (C2), 113.2 (C3'), 112.9 (C4'), 76.3 'C5), 71.6 (C13), 70.8 (C7), 70.0 (C6), 66.4 (C16), 61.4 (C11), 58.1 (C1'), 56.9 (C10), 43.9 (C4), 43.7 (C12), 41.6 (C8), 33.0 (C9), 20.4 (C14), 19.4 (C15), 12.2 (C17); m/e (relative intensity) 467 (M$^+$, 1%), 227 (22), 123 (100) (Found: 467.2155, C$_{23}$H$_{33}$NO$_9$ requires 467.2152).

EXAMPLE 8 m-Hydroxyiminomethylbenzyl monate A

A solution of m-formylbenzyl monate A (145 mg, 0.31 mmol), hydroxyamine hydrochloride (108 mg, 1.55 mmol) and ammonium acetate (124 mg, 1.55 mmol), in methanol (10 ml) and distilled water (10 ml) was stirred at 20° for 2 days. Brine was then added and the reaction mixture extracted three times with methylene chloride. The combined organic extracts were dried (MgSO$_4$), evaporated in vacuo and purified by chromatography (5 g silicagel, 0 to 6% methanol in methylene chloride) to yield a colourless oil (65 mg, 44%); $\nu_{max}$ (film) 3400, 1710, 1640 cm$^{-1}$; $\lambda_{max}$ (EtOH) 221 nm ($\epsilon_m$ 22,260); $\delta_H$ (CDCl$_3$) 8.12 (1H, s, C$\underline{H}$=NOH), 7.67-7.25 (4H, m, aryl), 5.82 (1H, s, H2), 5.10 (2H, s, CH$_2$), 2.20 (3H, s, CH$_3$-15), 1.17 (3H, d, CH$_3$-14) 0.85 (3H, d, CH$_3$-17).

Biological Data (a) Anti-Mycoplasmal Activity

Table 1 shows the in vitro MIC values ($\mu$g/ml) of the compounds of Examples 1 to 8 against a number of mycoplasma organisms. The values were determined in Friis broth solidified with 0.9% agarose. The inoculum was 10$^3$ to 10$^5$ C.F.U. and the MIC's were recorded after 6 days incubation at 37° C.

TABLE 1

| Organism | M.I.C. ($\mu$g/ml) COMPOUND OF EXAMPLE NUMBER | | | | | | | |
|---|---|---|---|---|---|---|---|---|
| | 1 | 2 | 3 | 4 | 5 | 6 | 7 | 8 |
| M. suipneumoniae NB12 | 0.1 | 0.25 | 0.5 | 0.25 | 0.25 | 0.5 | 1.0 | 0.25 |
| M. suipneumoniae JF 435 | 0.25 | 0.5 | 0.5 | 0.5 | 0.5 | 0.5 | 1.0 | 0.5 |
| M. suipneumoniae HK (2) | 0.25 | 0.5 | 0.5 | 0.5 | 0.5 | 1.0 | 1.0 | 0.5 |
| M. suipneumoniae Str. 11 | 0.1 | 0.25 | 0.25 | 0.25 | 0.25 | 0.5 | 0.5 | 0.25 |
| M. suipneumoniae J2206/183b | 0.25 | 0.5 | 0.5 | 0.5 | 0.5 | 1.0 | 1.0 | 0.5 |
| M. suipneumoniae MS16 | 0.1 | 0.25 | 0.25 | 0.25 | 0.25 | 0.25 | 0.5 | 0.25 |
| M. suipneumoniae PW/C/210 | 0.1 | 0.25 | 0.25 | 0.25 | 0.25 | 0.5 | 0.5 | 0.25 |
| M. suipneumoniae LABER | 0.1 | 0.25 | 0.25 | 0.25 | 0.25 | 0.5 | 0.5 | 0.25 |
| M. suipneumoniae UCD 1 | 0.25 | 0.5 | 0.5 | 0.5 | 0.25 | 1.0 | 1.0 | 0.5 |
| M. suipneumoniae TAM 6N | 0.25 | 0.5 | 0.5 | 0.5 | 0.5 | 1.0 | 1.0 | 0.5 |
| M. suipneumoniae ATCC 25095 | 0.25 | 0.25 | 0.5 | 0.5 | 0.5 | 0.5 | 0.5 | 0.25 |
| M. suipneumoniae NCTC 10110 | 0.25 | 0.5 | 0.5 | 0.5 | 0.25 | 0.5 | 1.0 | 0.5 |
| M. hyorhinis ATCC 23234 | 0.1 | 0.25 | 0.25 | 0.25 | 0.25 | 0.25 | 0.5 | 0.25 |
| M. hyorhinis ATCC 25021 | 0.1 | 0.25 | 0.25 | 0.25 | 0.25 | 0.25 | 0.5 | 0.25 |
| M. hyosynoviae ATCC 25591 | 0.25 | 0.5 | 0.1 | 0.25 | 0.25 | 0.1 | 0.25 | 0.25 |
| M. bovis NCTC 10131 | ≦0.01 | 0.05 | ≦0.01 | 0.025 | 0.025 | ≦0.01 | ≦0.01 | ≦0.01 |
| M. bovigenitalium ATCC 14173 | 0.025 | 0.1 | 0.025 | 0.05 | 0.05 | 0.025 | 0.025 | 0.025 |
| M. dispar NCTC 10125 | 0.05 | 0.1 | 0.1 | 0.1 | 0.1 | 0.25 | 0.1 | 0.1 |
| M. gallisepticum S6 | 10 | 10 | 5.0 | 10 | 10 | 5.0 | 5.0 | 5.0 |

TABLE 1-continued

| Organism | M.I.C. (μg/ml) COMPOUND OF EXAMPLE NUMBER | | | | | | | |
|---|---|---|---|---|---|---|---|---|
| | 1 | 2 | 3 | 4 | 5 | 6 | 7 | 8 |
| M. pneumoniae ATCC 15492 | 2.5 | 2.5 | 1.0 | 2.5 | 2.5 | 2.5 | NG | 2.5 |

NG - Organism failed to grow in test (b) Veterinary Bacteria

Table 2 shows the MIC values (μg/ml) of the compounds of Examples 1 to 8 against a number of organisms important in veterinary infections. The values were determined using a two fold serial dilutions in Diagnostic Sensitivity Test Agar with an inoculum of 10⁴ organisms and incubation for 18 hours at 37° C.

TABLE 2

| Organism | M.I.C. (μg/ml) COMPOUND OF EXAMPLE NUMBER | | | | | | | |
|---|---|---|---|---|---|---|---|---|
| | 1 | 2 | 3 | 4 | 5 | 6 | 7 | 8 |
| E. coli NCTC 10418 | >80 | >80 | >80 | >80 | >80 | >80 | >80 | |
| E. coli El | >80 | >80 | >80 | >80 | >80 | >80 | >80 | |
| S. dublin S7 | >80 | >80 | >80 | >80 | >80 | >80 | >80 | |
| S. typhimurium S18 | >80 | >80 | >80 | >80 | >80 | >80 | >80 | |
| Bord. bronchiseptica B08 | 40 | >80 | >80 | >80 | >80 | 5 | >80 | |
| Bord. brochiasetpica B09 | 20 | 80 | 20 | 5 | 40 | 2.5 | 2.5 | |
| Past. multocida PA1 | 2.5 | 20 | 1.25 | 2.5 | 20 | 2.5 | .625 | |
| Past. multocida PA2 | .625 | 5 | .312 | 0.156 | 0.039 | .312 | .625 | |
| Past. haemolytica PA5 | 10 | 80 | 5 | 20 | 30 | 10 | 5 | |
| Erysipelothrix rhusiopathiae NCTC 8163 | 20 | 10 | 10 | 20 | 40 | 80 | >80 | |
| Corynebacterium pyogenes CY1 | >80 | >80 | >80 | >80 | >80 | >80 | >80 | |
| Staph. aureus B4 (pen. resistant) | .625 | 10 | 2.5 | 0.625 | 0.625 | .07 | 1.25 | |
| Staph. aureus 152 (pen. sens) | .625 | 5 | 1.25 | 0.312 | 0.625 | .07 | 1.25 | |
| Staph. aureus Oxford | .625 | 5 | 1.25 | 0.312 | 0.625 | .07 | 1.25 | |
| Strep. suis (Group D) SPS11 | 5 | 10 | 2.5 | 10 | 20 | 20 | 20 | |
| Strep. uberis SPU1 | .156 | .625 | .156 | 0.312 | 0.625 | .312 | .625 | |
| Strep. dysgalactiae SPD1 | .625 | .625 | .312 | 0.625 | 1.25 | .07 | .625 | |
| Strep. agalactiae SPA1 | .625 | 2.5 | .625 | 0.625 | 1.25 | 1.25 | 1.25 | |
| B subtilis ATCC 6633 | — | — | — | — | NG | NG | NG | |

(c) Human Bacteria

Table 3 shows the MIC values (μg/ml) of the compounds of Examples 1 to 8 against a number of organisms important in human infections. The values were determined by serial dilutions in nutrient agar with 5% chocolated horse blood after incubations for 18 hours at 37° C.

TABLE 3

| Organism | M.I.C. (μg/ml) COMPOUND OF EXAMPLE NUMBER | | | | | | | |
|---|---|---|---|---|---|---|---|---|
| | 1 | 2 | 3 | 4 | 5 | 6 | 7 | 8 |
| E. Coli NCT 10418 | >100 | >100 | >100 | >100 | >100 | >100 | >100 | |
| E. coli ESS | 2.5 | 5 | 1.0 | 2.5 | 5.0 | 5 | 2.5 | |
| P. mirabilis 889 | >100 | >100 | >100 | >100 | >100 | >100 | >100 | |
| K. aerogenes A | >100 | >100 | >100 | >100 | >100 | >100 | >100 | |
| Ps. aeruginosa 10662 | >100 | 100 | >100 | >100 | >100 | >100 | >100 | |
| Pasteurella multocida 1633 | 5.0 | 10.0 | 1.0 | 5.0 | 50 | 1.0 | 2.5 | |
| Haemophilus influenzae Q1 | 0.5 | — | 0.25 | 0.5 | 2.5 | 0.5 | 0.25 | |
| Haemophilus influenzae Wy21 | 0.5 | 1.0 | — | — | — | 0.5 | 0.25 | |
| Neisseria catarralis 1502 | 0.2 | 1.0 | 1.0 | 0.5 | 1.0 | 0.05 | 0.25 | |
| Bacillus subtilis 6633 | 1.0 | 2.5 | 1.0 | 1.0 | 1.0 | 5 | 1.0 | |
| Corneybacterium xerosis 9755 | NG | >100 | >100 | >100 | >100 | >100 | >100 | |
| Sarcina lutea 8340 | NG | — | >100 | >100 | >100 | >100 | >100 | |
| Staph. aureus Oxford | 2.5 | 5 | 2.5 | 1.0 | 1.0 | 0.1 | 2.5 | |
| Staph. aureus Russell | 2.5 | 10 | 5.0 | 2.5 | 2.5 | 0.25 | 2.5 | |
| Staph. aureus W2827 | 2.5 | 10 | 5.0 | 2.5 | 2.5 | 0.25 | 5.0 | |
| Strep. faecalis I | >100 | >100 | 25 | 100 | >100 | >100 | >100 | |
| Strep. pyogenes R80/421 | 2.5 | 2.5 | 0.5 | 1.0 | 2.5 | 1.0 | 1.0 | |
| Strep Group B 2788 | 2.5 | 2.5 | 1.0 | 2.5 | 5.0 | 1.0 | 2.5 | |
| Strep. Group C 64/848 | 2.5 | 5 | 1.0 | 1.0 | 2.5 | 1.0 | 2.5 | |
| Strep. pneumoniae CN33 | 0.5 | 1.0 | 0.5 | 1.0 | 2.5 | 1.0 | 2.5 | |

(d) Serum binding

Serum binding was assessed by ultrafiltration of porcine serum containing compounds at 8 mcg/ml, and through an Amicon CF50A ultrafiltration cone. Separation of ultrafiltrate was achieved by centrifugation. Unbound concentrations of compound were measured in the ultrafiltrate by microbiological assay (B. subtilis ATCC 6633) against standards prepared in saline.

| Compound of Example No. | % bound to pig serum. |
|---|---|
| 1 | >92 |
| 2 | >84.1 |
| 3 | 64.5 |
| 4 | >96.1 |
| 5 | >93.2 |
| 6 | 76.1 |

(e) Mouse blood levels of Examples 1, 3 & 6 following their oral and subcutaneous administration Blood levels were assessed in albino male mice (18–22 g strain OLAC:MF-1). The dose was 50 mg/kg administered in a 10% ethanol solution orally and subcutaneously. The mice were killed at intervals and up to 1½ hours and the blood assayed microbiologically using M. bovis ATCC 25025 or B. subtilis.

| Example | Route of Administration | conc. μg/ml at mins after dosing | | | | | | |
|---|---|---|---|---|---|---|---|---|
| | | 5 | 10 | 20 | 30 | 45 | 60 | 90 |
| 1 | Subcutaneous | 4.4 | 6.5 | 3.1 | 1.6 | 0.46 | 0.28 | <0.2 |
| | Oral | 1.0 | 0.79 | 0.23 | <0.2 | <0.2 | <0.12 | <0.2 |
| 3 | Subcutaneous | 20.6 | 23.0 | 16.6 | 7.9 | 2.9 | 1.5 | 0.3 |
| | Oral | 3.5 | 3.5 | 2.2 | 1.9 | 1.6 | 0.8 | 0.6 |
| 6 | Subcutaneous | 12.1 | 14.8 | 9.7 | 6.8 | 3.8 | 2.3 | <0.6 |
| | Oral | 3.4 | 3.4 | 0.68 | <0.6 | <0.6 | <0.6 | <0.6 |

(f) Mean serum concentrations in neonatal piglets after intramuscular or oral administrations at 50 mg/mg of Example 1

Blood levels were assessed in neonatal piglets (2 to 4 animals per group and mean bodyweights about 2 kg). The dose was 50 mg/kg (dose solution = 25 mg/ml in 25% ethanol). Doses were given by intramuscular injection and orally by stomach tube. Piglets were held at intervals up to 6 and at 24 hours, serum assayed microbiologically (*B. subtilis* ATCC 6633).

| Compound of Example No. | Route of Administration. | serum concentrations (μg/ml) at: | | | | | | | |
|---|---|---|---|---|---|---|---|---|---|
| | | 10' | 20' | 40* | 1h | 2h | 3h | 4h | 6h | 24h |
| 1 | i.m. | 7.0 | 6.7 | 6.3 | 6.6 | 5.2 | 2.9 | 1.7 | <0.9 | — |
| | p.o. | 3.0 | 3.0 | 3.3 | 1.2 | <1.0 | — | — | — | — |

'represents minutes

We claim:

1. A compound of formula (II)

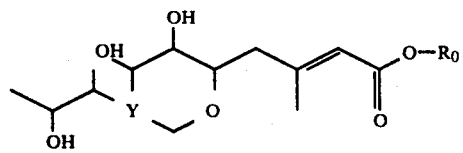

in which Y represents

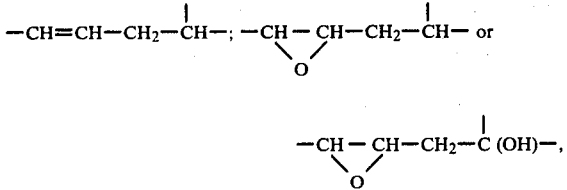

and $R_0$ represents $C_{2-20}$ alkyl, $C_{3-8}$ cycloalkyl, $C_{4-20}$ alkenyl, phenylalkyl, cycloalkylalkyl, heterocyclyl or heterocyclylalkyl wherein said heterocyclyl is a five or six-membered heterocyclic ring containing oxygen, sulfur or nitrogen as the sole heteroatom, said heterocyclic ring being unsubstituted or substituted by lower alkyl, which is substituted by a hydroxyimino-, hydrazono- or semicarbazono group.

2. A compound according to claim 1, in which the hydroxyimino-, hydrazono- or semicarbazono- group is substituted by one or more $C_{1-6}$ alkyl or phenyl, unsubstituted or substituted by one or more bromo or nitro.

3. A compound according to claim 1 in which $R_0$ represents a group of the formula (III):

 (III)

in which W represents a

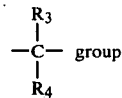 group where $R_3$ and $R_4$ are the same or different and each is hydrogen, $C_{1-4}$ alkyl, phenyl, or phenylalkyl, Z represents $(CH_2)_n$, where n is an integer of from 1 to 10 or is zero, or $C_6H_4$, $R_1$ represents a hydroximino-, hydrazono- or semicarbazono group each of which is unsubstituted or substituted by one or more $C_{1-6}$ alkyl or phenyl, said $C_{1-6}$ alkyl and said phenyl being unsubstituted or substituted by bromo or nitro, and $R_2$ represents hydrogen, $C_{1-4}$ alkyl, phenyl or a five or six-membered heterocyclic ring containing oxygen, sulfur or nitrogen as the sole heteroatom, said heterocyclic ring being unsubstituted or substituted by lower alkyl.

4. A compound selected from:
4-Hydroxyimino-4-phenylbutyl monate A
4-Phenyl-4-semicarbazonobutyl monate A
4-Hydroxyiminocyclohexyl monate A
4-Hydroxyimino-4-(2-thienyl)butyl monate A
4-Methoxyimino-4-phenylbutyl monate A
6-Dimethylhydrazonohexyl monate A
5-Hydroxyiminomethylfurfuryl monate A, and
m-Hydroxyiminomethylbenzyl monate A.

5. An antibacterial or antimycoplasmal, pharmaceutical or veterinary composition comprising an effective, non-toxic amount of a compound of formula (II) as defined in claim 1 and a pharmaceutically or veterinarily acceptable carrier therefor.

6. A method for treating humans or animals which comprises administering an antibacterially or antimycoplasmally effective non-toxic amount of a compound of formula (II) as defined in claim 1 to a human or animal suffering from a bacterial or mycoplasmal infection.

7. A compound according to claim 1, wherein said heterocyclic ring is thienyl or furyl, unsubstituted or substituted by lower alkyl.

* * * * *